United States Patent
Bogdan et al.

(10) Patent No.: US 8,134,037 B2
(45) Date of Patent: *Mar. 13, 2012

(54) XYLENE ISOMERIZATION PROCESS AND APPARATUS

(75) Inventors: Paula L. Bogdan, Mount Prospect, IL (US); Robert B. Larson, Lisle, IL (US); James E. Rekoske, Glenview, IL (US); Patrick J. Silady, Niles, IL (US); Patrick C. Whitchurch, Bossier City, LA (US); Freddie Sandifer, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 198 days.

This patent is subject to a terminal disclaimer.

(21) Appl. No.: 12/614,780

(22) Filed: Nov. 9, 2009

(65) Prior Publication Data

US 2010/0069694 A1    Mar. 18, 2010

Related U.S. Application Data

(60) Continuation-in-part of application No. 11/829,225, filed on Jul. 27, 2007, now abandoned, which is a division of application No. 11/299,579, filed on Dec. 12, 2005, now Pat. No. 7,371,914.

(51) Int. Cl.
C07C 5/22        (2006.01)
C10G 35/00       (2006.01)
C10G 35/04       (2006.01)
B01J 8/02        (2006.01)
B01J 35/02       (2006.01)

(52) U.S. Cl. ........ 585/481; 585/477; 585/480; 208/133; 208/134; 422/211

(58) Field of Classification Search .............. 585/477, 585/481, 480; 208/134, 133; 422/211
See application file for complete search history.

(56) References Cited

U.S. PATENT DOCUMENTS

| | | | |
|---|---|---|---|
| 3,548,017 A | 12/1970 | Hebert et al. | |
| 4,899,012 A | 2/1990 | Sachtler et al. | |
| 6,198,014 B1 * | 3/2001 | Alario et al. | 585/480 |
| 6,271,429 B1 | 8/2001 | Joly et al. | |
| 6,576,581 B1 * | 6/2003 | Sharma et al. | 502/66 |
| 7,371,914 B1 * | 5/2008 | Larson et al. | 585/481 |
| 2008/0041765 A1 | 2/2008 | Larson et al. | |
| 2008/0217247 A1 * | 9/2008 | Niino et al. | 210/651 |

OTHER PUBLICATIONS

U.S. Appl. No. 11/829,225, filed Jul. 27, 2007, Robert B. Larson et al., Amendment After Non-Final Rejection dated Sep. 17, 2009.
U.S. Appl. No. 11/829,225, filed Jul. 27, 2007, Robert B. Larson et al., USPTO Office Action mailed Jun. 17, 2009.
U.S. Appl. No. 11/829,225, filed Jul. 27, 2007, Robert B. Larson et al.

* cited by examiner

*Primary Examiner* — Walter D Griffin
*Assistant Examiner* — Natasha Young
(74) *Attorney, Agent, or Firm* — Mark R Willis

(57) ABSTRACT

Xylene isomerization processes, especially those processes in which ethylbenzene is also converted, are beneficially affected by adding benzene to the feed.

9 Claims, 2 Drawing Sheets

XYLENE ISOMERIZATION PROCESS AND APPARATUS

CROSS REFERENCE TO RELATED APPLICATIONS

This application is a Continuation-In-Part of application Ser. No. 11/829,225 filed Jul. 27, 2007, which in turn is a Division of application Ser. No. 11/299,579 filed Dec. 12, 2005, now U.S. Pat. No. 7,371,914, the contents of which are hereby incorporated by reference in their entirety.

FIELD OF THE INVENTION

This invention relates to improved processes for the catalytic isomerization of a non-equilibrium mixture of one or more xylenes including isomerization processes associated with the conversion of ethylbenzene and apparatus therefor.

BACKGROUND OF THE INVENTION

The xylenes, para-xylene, meta-xylene and ortho-xylene, are important intermediates which find wide and varied application in chemical syntheses. Para-xylene upon oxidation yields terephthalic acid which is used in the manufacture of synthetic textile fibers and resins. Meta-xylene is used in the manufacture of plasticizers, azo dyes, wood preservers, etc. Ortho-xylene is feedstock for phthalic anhydride production.

Xylene isomers from catalytic reforming or other sources generally do not match demand proportions as chemical intermediates, and further comprise ethylbenzene which is difficult to separate or to convert. Para-xylene in particular is a major chemical intermediate. Adjustment of isomer ratio to demand can be effected by combining xylene-isomer recovery, such as adsorption for para-xylene recovery, with isomerization to yield an additional quantity of the desired isomer. Isomerization converts a non-equilibrium mixture of the xylene isomers which is lean in the desired xylene isomer to a mixture which approaches equilibrium concentrations.

Various catalysts and processes have been developed to effect xylene isomerization. Catalysts for isomerization of $C_8$ aromatics ordinarily are classified by the manner of processing ethylbenzene associated with the xylene isomers. Ethylbenzene is not easily isomerized to xylenes, but it normally is converted in the isomerization unit because separation from the xylenes by superfractionation or adsorption is very expensive. One approach is reacting ethylbenzene to form a xylene mixture via conversion to and reconversion from naphthenes in the presence of a solid acid catalyst with a hydrogenation-dehydrogenation function. An alternative, widely-used approach is to dealkylate ethylbenzene to form principally benzene while isomerizing xylenes to a near-equilibrium mixture. The former approach enhances xylene yield by forming xylenes from ethylbenzene, while the latter approach commonly results in higher ethylbenzene conversion, thus lowering the quantity of recycle to the para-xylene recovery unit and concomitant processing costs.

Crystalline aluminosilicate zeolite-containing catalysts have become prominent for xylene isomerization. U.S. Pat. No. 3,856,872, for example, teaches xylene isomerization and ethylbenzene conversion with a catalyst containing ZSM-5, -12, or -21 zeolite. U.S. Pat. No. 4,626,609 discloses conversion of xylene isomers using a catalyst comprising a composite which has been steamed at 200° to 500° C. U.S. Pat. No. 4,899,012 discloses the use of a catalyst containing lead, a Group VIII metal, a pentasil zeolite and an inorganic-oxide binder to isomerize xylenes and dealkylate ethylbenzene. Development efforts continue toward realizing economically attractive isomerization catalysts with a superior combination of activity, selectivity and stability.

Of concern in isomerization processes is the loss of xylenes. The major loss of xylenes is believed to result from the disproportionation of xylene to toluene and trimethylbenzene. U.S. Pat. No. 5,998,688 proposes a xylene isomerization process preferably using a ZSM-5-containing catalyst with a toluene co-feed. The patentees state that the feedstock to the isomerization contains 1 to 25 percent toluene by weight, and that increasing the toluene concentration minimizes the loss of xylenes during the ethylbenzene conversion stage. Nevertheless, in the sole example, the addition of toluene to provide a feed containing 18.7 weight percent toluene, resulted in an increase of trimethylbenzene which is inconsistent with the objective of reducing xylene ring loss. The mass ratio of $C_9+$ to $C_8$ aromatics more than doubles between the described control and the toluene-co-feed examples.

The presence of toluene in feeds to xylene isomerization processes has been disclosed by others subsequently. Benzene and toluene can be present in the non-equilibrium xylene mixtures, including in commercially operating para-xylene and ortho-xylene production facilities. Examples III and IV of U.S. Pat. No. 6,576,581 disclose xylene isomerization of a feed containing 1.53 and 0.78 mass-% toluene plus benzene.

U.S. Pat. No. 6,198,014 discloses a process for isomerizing $C_8$ aromatic compounds involving adding hydrogen and a recycle mixture to the $C_8$ aromatic feed to the isomerization reactor. The recycle is said to comprise at least one acyclic $C_8$ paraffin, at least one $C_8$ naphthene, at least benzene and at least toluene and is said to be devoid of $C_8$ aromatic compounds and paraffins of 1 to 7 carbons. The patentees state that the recycle mixture provides benefits of reducing the production of paraffins, naphthenes and $C_9$ and higher aromatics as well as reducing the loss of $C_8$ aromatics by secondary side reactions of dismutation, transalkylation, hydrogenation and cracking Examples 5 and 6 in the patent use feeds containing, inter alia, 0.1 weight percent benzene and toluene, 2.0 and 2.9 weight percent respectively.

SUMMARY OF THE INVENTION

In accordance with this invention, improved processes for xylene isomerization using molecular sieve-containing isomerization catalyst are provided, in which processes benzene is added. The added benzene can beneficially affect one or more isomerization and ethylbenzene conversion, if ethylbenzene is present, properties including: (i) enhancing isomerization activity to achieve a closer approach to equilibrium; (ii) enhancing the conversion of ethylbenzene; (iii) reducing xylene loss; and (iv) reducing trimethylbenzene. The beneficial effects are with observed through comparison with a substantially identical process but without the additional benzene. A substantially identical process is one that has approximately the same weighted average bed temperature, operating pressure and hourly space velocity is the same reactor using the same catalyst (the activity and selectivity of which have not been materially changed such as by use or poisoning) at steady state conditions.

The isomerization processes of this invention are applicable to xylene isomerization processes with and without associated ethylbenzene conversion. Associated ethylbenzene conversion processes include those in which the ethylbenzene conversion is conducted during the isomerization as well as those in which the ethylbenzene conversion is primarily conducted in a different catalytic reaction zone after, or preferably before, the catalytic reaction zone for the xylene isomerization. The ethylbenzene conversion processes can be those in which the ethylbenzene is converted to xylenes or, preferably, those in which ethylbenzene is dealkylated. Typically, isomerization and ethylbenzene processes generate benzene as a by-product, especially where ethylbenzene is in the feed to the isomerization and dealkylation of ethylbenzene occurs. In this invention, the benzene concentration is in addition to any benzene that would be generated in the isomerization and ethylbenzene conversion process.

In one broad aspect, the processes of this invention for isomerizing a feed stream containing a non-equilibrium mixture at least one xylene, and optionally ethylbenzene, comprise:

a. providing in at least a portion of the feed stream benzene in an amount sufficient to beneficially affect at least one of isomerization and ethylbenzene conversion, if ethylbenzene is present, often between about 0.5 and 25 mass percent of the feed, and b. subjecting the feed stream containing the provided benzene to isomerization, and optionally ethylbenzene, conversion conditions to provide a product stream having a redistributed xylenes ratio.

Preferably, the feed stream contains ethylbenzene and ethylbenzene is dealkylated during isomerization.

Preferred isomerization conditions comprise a temperature of from about 100° to 600° C., a pressure of from about 10 kPa to 5 MPa, a mass hourly space velocity of from about 0.5 to 100 hr$^-$. Operation at a temperature of between 150° to 500° C. and at a mass hourly space velocity of from about 1 to 50 hr$^{-1}$ is especially favored. Preferred catalysts for isomerization and for ethylbenzene conversion comprise pentasil zeolites.

Preferably, benzene is selectively separated, e.g., by distillation or selective permeation, from at least a portion of the product stream is to recover benzene and at least a portion of the benzene is used as provided benzene.

The broad aspects of the apparatus of this invention comprise:

a. a reaction assembly having at least one feedstream inlet and at least one product outlet containing therebetween at least one reaction zone wherein at least one reaction zone contains catalyst suitable for the conversion of ethylbenzene and the same or at least one other reaction zone contains catalyst suitable for the isomerization of xylenes;

b. a distillation assembly in fluid communication at an inlet with the product outlet of the reaction assembly, said distillation assembly having an outlet adapted to provide a benzene-containing stream, said outlet being in fluid communication with at least one feedstream inlet of the reaction assembly.

DETAILED DESCRIPTION OF THE INVENTION

Figure 1:
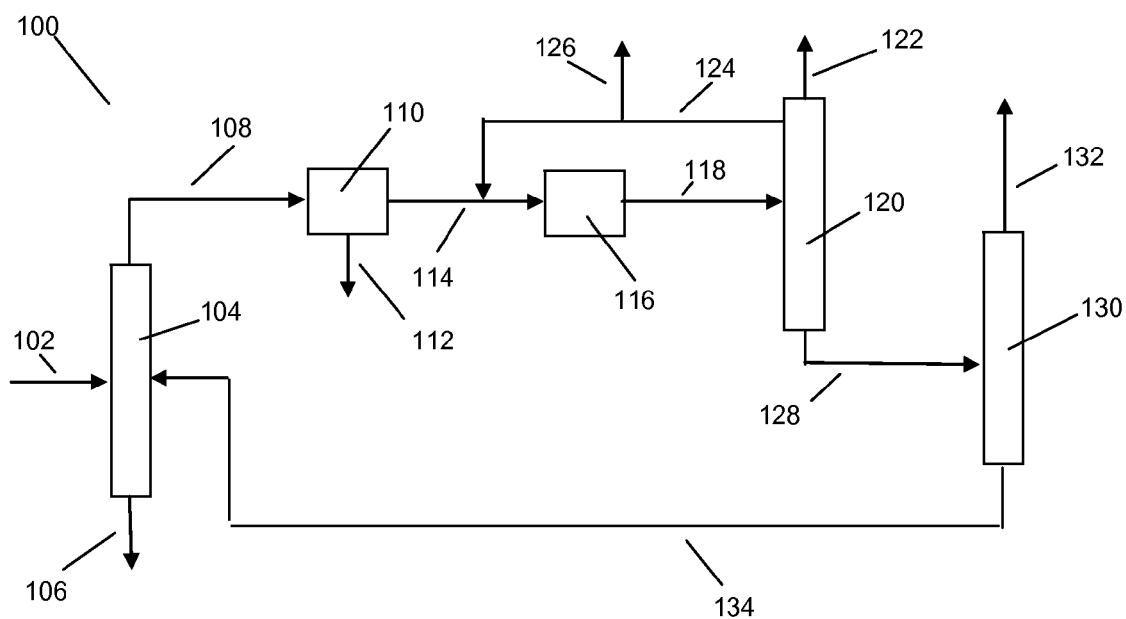
FIG. 1 is a schematic depiction of an apparatus of this invention in which benzene is recovered from the isomerization product and a portion is recycled to the reaction assembly.

The feed stream for aromatics isomerization is typically a $C_8$ aromatics stream from which one or more xylenes have been removed as product. Usually the $C_8$ aromatics stream is prepared by removal of at least one of para- and ortho-xylene from a fresh $C_8$ aromatics feed obtained from processes, such as catalytic reforming and extraction, for the production and recovery of aromatics from other hydrocarbons. See, for instance, Robert A. Meyers, *Handbook of Petroleum Refining Processes, Second Edition*, McGraw-Hill, 1997, Part 2. Most commercial facilities recover from a $C_8$ aromatics stream at least para-xylene, and sometimes also ortho-xylene, as products and isomerize the remaining $C_8$ aromatics to recover more of the para-xylene, and ortho-xylene if applicable. Consequently, the feed streams may be relatively free from non-aromatics and from higher and lower molecular weight aromatics. Alternatively, the feed stream may contain naphthenes and other hydrocarbons such as paraffins usually in an amount up to 30 mass-percent. Preferably the isomerizable hydrocarbons consist essentially of aromatics, however, to ensure pure products from downstream recovery processes.

The feed stocks to the aromatics isomerization process of this invention comprise non-equilibrium xylene and, most frequently, ethylbenzene. These aromatic compounds are in a non-equilibrium mixture, i.e., at least one $C_8$ aromatic isomer is present in a concentration that differs substantially from the equilibrium concentration at isomerization conditions. Thus, a non-equilibrium xylene composition exists where one or two of the xylene isomers are in less than equilibrium proportion with respect to the other xylene isomer or isomers. The xylene in less than equilibrium proportion may be any of the para-, meta- and ortho-isomers. As the demand for para- and ortho-xylenes is greater than that for meta-xylene, usually, the feed stocks will contain meta-xylene. Generally the mixture will have an ethylbenzene content of about 1 to about 60 mass-percent, an ortho-xylene content of 0 to about 35 mass-percent, a meta-xylene content of about 20 to about 95 mass-percent and a para-xylene content of 0 to about 30 mass-percent. Usually the non-equilibrium mixture is prepared by removal of one or more of para-, ortho- and meta-xylene from a fresh $C_8$ aromatic mixture obtained from an aromatics-production process.

In the processes of this invention benzene is provided to a xylene-containing feed for isomerization, and optionally ethylbenzene conversion. As stated above, the amount of benzene provided is sufficient to obtain one or more beneficial effects in the isomerization and ethylbenzene conversion, if ethylbenzene is present.

In one aspect of the processes of this invention, the beneficial effect of the provided benzene is an enhancement of xylene isomerization activity. For processes in which para-xylene is the sought product, the provided benzene is preferably in an amount sufficient to increase the mole percentage of para-xylene to total xylenes by at least about 0.1, and more preferably, by at least about 0.15, percentage points, as compared to substantially the same process but not containing the provided benzene. Typically the benzene is provided in an amount of between about 0.5 and 15, more preferably between about 1 and 12, mass percent based upon the mass of the feed.

In another aspect of the processes of this invention, the beneficial effect of the provided benzene is an enhancement of the conversion of ethylbenzene, especially where the conversion is a dealkylation conversion. The amount of provided benzene is preferably in an amount sufficient to increase the conversion by at least about 3, preferably at least about 5, percentage points at approximately the same weighted average bed temperature as compared to a substantially identical process but not containing the provided benzene. For this comparison, the weighted average bed temperature for the comparative process is sufficient to provide an ethylbenzene conversion between about 10 and 30 percent for conversion processes generating xylenes, and between about 60 and 75 percent for ethylbenzene dealkylation processes. Typically the benzene is provided in an amount of between about 0.5 and 15, more preferably between about 1 and 12, mass percent based upon the mass of the feed.

In yet another aspect of the processes of this invention, the beneficial effect of the provided benzene is a reduction in xylene loss. The amount of provided benzene is preferably in an amount sufficient to reduce the xylene loss by at least about 0.3, preferably at least about 0.5, percentage points at approximately the same weighted average bed temperature as compared to a substantially identical process but not containing the provided benzene. For this comparison, the weighted average bed temperature for the comparative process is sufficient to provide an ethylbenzene conversion between about 10 and 30 percent for conversion processes generating xylenes, and between about 60 and 75 percent for ethylbenzene dealkylation processes. Typically the benzene is provided in an amount of between about 0.5 and 25, more preferably between about 1 and 20, and often between about 5 and 20, mass percent based upon the mass of the feed.

In a further aspect of the processes of this invention, the beneficial effect of the provided benzene is a reduction in trimethylbenzene make. The amount of provided benzene is preferably in an amount sufficient to reduce the trimethylbenzene make by at least about 0.1, preferably at least about 0.2, percentage points at approximately the same weighted average bed temperature as compared to a substantially identical process but not containing the provided benzene. For this comparison, the weighted average bed temperature for the comparative process is sufficient to provide an ethylbenzene conversion between about 10 and 30 percent for conversion processes generating xylenes, and between about 60 and 75 percent for ethylbenzene dealkylation processes. Typically the benzene is provided in an amount of between about 5 and 25, more preferably between about 10 and 20, mass percent based upon the mass of the feed.

The optimal amount of benzene to be provided will depend upon the nature of the benefit sought to be achieved. For instance, where increases in isomerization activity and/or ethylbenzene conversion activity are sought, the optimal benzene provided will typically range from about 2 to 8 mass percent of the feed. As the amount of benzene is increased above that amount, the activity decrease, and at much higher levels of provided benzene, the activities may be less than that in the absence of benzene. On the other hand, where the reduction in xylene ring loss is the primary focus, the optimal amount of provided benzene is often greater, e.g., greater than about 5 or 7 mass percent. Reduction in trimethylbenzene co-production usually requires even more provided benzene. Hence, for a given xylene isomerization process, the artisan, having the benefit of this invention, can select the amount of provided benzene to achieve an overall optimal combination of benefits suitable for that production facility, production economics and the market demands.

The multiple benefits that can be achieved using the processes of this invention can be reaped by the artisan in a number of ways. For example, a xylene production facility having fresh catalyst may be operated with greater amounts of provided benzene to take as a primary benefit a reduction in xylene ring loss. As the catalyst ages, the amount of benzene provided can be reduced to achieve a desired isomerization and ethylbenzene conversion activity. In another mode of capturing value, the addition of benzene can debottleneck a xylene isomerization reactor.

It should also be kept in mind that the optimal amount of benzene to be provided will depend upon the specific process and process conditions used as well as the concentration of ethylbenzene in the feed stream and the extent of conversion of the ethylbenzene. By way of example, in an isomerization process that dealkylates 70 percent of the ethylbenzene, more benzene will be produced than a process that only dealkylates 50 percent of the ethylbenzene, all other things being constant. Similarly, a feed containing 20 mass-percent ethylbenzene will generate more benzene than a feed containing 10 mass-percent ethylbenzene, all other things being constant.

In preferred aspects of this invention, little or no toluene is added to the feed stream. Toluene can reduce the benefits provided by adding benzene. Preferably, the mass ratio of toluene to benzene in the feed stream is less than about 1:1. In another preferred aspect of the invention, toluene is present in an amount less than about 2 mass percent based upon the entire feed.

The benzene may be provided prior to the contacting of the feed stream with the isomerization catalyst, or alternatively, all or a portion of the added benzene may be added during contacting with the isomerization catalyst. For instance, the isomerization zone may be composed of two or more stages containing catalyst and benzene may be admixed with the fluid passing between stages. Where one stage primarily effects ethylbenzene conversion and another stage primarily effects xylene isomerization, the locations at which benzene is added can contribute to the performance of the unit. For example, the xylene isomerization may precede the ethylbenzene conversion and an isomerization enhancing amount of benzene may be added to the feed to the isomerization and more benzene added to the isomerization product to achieve a reduction in xylene ring loss during the ethylbenzene conversion.

The $C_8$ aromatics-containing feed stream is contacted with the isomerization catalyst at suitable xylene-isomerization conditions. The processes of this invention are broadly applicable to catalytic xylene isomerization processes. The preferred processes are those in which the feed stream contains ethylbenzene and ethylbenzene is reacted, e.g., by dealkylation or by conversion to xylenes. The catalysts and reaction conditions will be dependent upon the type of isomerization being conducted and, if ethylbenzene is to be reacted, the type of reaction for the ethylbenzene.

The processes often involve a temperature ranging from about 100° to 600° C. or more, preferably in the range of from about 370° to 500° C. The pressure generally is from about 100 kPa to 10 MPa, and more usually no more than about 5 MPa. Sufficient catalyst is contained in the isomerization zone to provide a mass hourly space velocity with respect to the hydrocarbon feed mixture of from about 0.5 to 100 $hr^{-1}$, and preferably 1 to 50 $hr^{-1}$. Hydrogen is usually present in a hydrogen/hydrocarbon ($C_8$ aromatics) mole ratio of about 0.5:1 to about 10:1 or more; other inert diluents such as nitrogen, argon and light hydrocarbons may also be present. Where ethylbenzene conversion to xylenes is sought, the process conditions also include the presence of naphthenes, e.g., in amounts of between about 1 and 15 or more mass percent of the feed. Where multiple reaction zones are used, process conditions can vary among the reaction zones. Advantageously, the process conditions such as temperature and pressure are the same or close in each of the reaction zones for sake of avoiding heat exchange, compression or other unit operations.

The process conditions include the presence of solid, molecular sieve-containing catalyst. The $C_8$ aromatics-containing feed stream, preferably in admixture with hydrogen, is contacted with a molecular sieve-containing catalyst in an isomerization zone. Contacting may be effected using the catalyst in a fixed-bed system, a moving-bed system, a fluidized-bed system, or in a batch-type operation. In view of the danger of attrition loss of the valuable catalyst and of the simpler operation, it is preferred to use a fixed-bed system. In this system, a hydrogen-rich gas and the feed mixture are preheated by suitable heating means to the desired reaction temperature and then passed into an isomerization zone containing a fixed bed of catalyst. The conversion zone may be one or more separate reactors with suitable means therebetween to ensure that the desired isomerization temperature is maintained at the entrance to each zone.

The reactants may be contacted with the catalyst bed in either upward-, downward-, or radial-flow fashion, and the reactants may be in the liquid phase, a mixed liquid-vapor phase, or a vapor phase when contacted with the catalyst.

The isomerization product contains xylenes in a redistributed ratio. Where the feed contains ethylbenzene, the product will contain a reduced concentration of ethylbenzene as compared to that in the $C_8$ aromatics-containing feed stream. The amount of reduction will depend upon the type of ethylbenzene conversion. For conversion processes in which xylene are produced, the amount of ethylbenzene in the isomerization product will be reduced by at least about 5, preferably between 10 and 50, mass percent as compared to the amount in the feed. For dealkylation processes, the amounts of ethylbenzene in the isomerization product will often be reduced by at least about 20, and sometimes between about 25 and 90, and most often between about 50 and 80, mass-percent from the amounts in the feed stream. The ratio of the xylene isomers in the isomerization product preferably approaches equilibrium at the conditions of the isomerization, e.g., at least about 80, and more preferably at least about 90, percent of equilibrium. Typically, the mass ratio of para-xylene to total xylenes is between about 0.2:1 to 0.25:1, preferably between about 0.23 to 25:1, say, 0.235 to 25:1.

The particular scheme employed to recover an isomerized product from the effluent of the reactors of the isomerization zone is not deemed to be critical to the instant invention, and any effective recovery scheme known in the art may be used. Typically, the reactor effluent is condensed and the hydrogen and light-hydrocarbon components removed therefrom by flash separation. The condensed liquid product then is fractionated to remove light and/or heavy byproducts and obtain the isomerized $C_8$ aromatics product which can be recycled for recovery of para-xylene and, if desired, ortho-xylene.

In most commercial processes, facilities exit for removal of benzene from the isomerization product such that the $C_8$ aromatics-containing stream which is recycled for separation of the sought xylene isomer contains little, if any benzene. As mentioned above, benzene is strongly sorbed on sorbent used to separate para-xylene and is not easily desorbed, thus the removal of benzene is required. Typically the removal is effected by distillation. In the processes of this invention, at least a portion of the benzene-containing stream from this separation is recycled to the isomerization step as provided benzene. Advantageously, the toluene to benzene mass ratio in this recycle stream is less than about 1:1, and preferably is less than about 1:4.

Typical catalysts contain a catalytically-effective amount of molecular sieve having a pore diameter of from about 4 to 8 Å and a catalytically-effective amount of one or more hydrogenation metal components. Examples of molecular sieves include those having $Si:Al_2$ ratios greater than about 10, and often greater than about 20, such as the MFI, MEL, EUO, FER, MFS, MTT, MTW, TON, MOR, UZM-8 and FAU types of zeolites. Pentasil zeolites such as MFI, MEL, MTW and TON are preferred, and MFI-type zeolites, such as ZSM-5, silicalite, Borolite C, TS-1, TSZ, ZSM-12, SSZ-25, PSH-3, and ITQ-1 are especially preferred. The catalysts may contain hydrogenation metal components and may contain suitable binder or matrix material such as inorganic oxides and other suitable materials. The relative proportion of zeolite in the catalyst may range from about 10 to about 99 mass-percent, with about 20 to about 90 mass-percent being preferred. There is a tradeoff between the zeolite content of the catalyst composite and the pressure, temperature and space velocity of an isomerization operation in maintaining low xylene ring losses.

A refractory binder or matrix is typically used to facilitate fabrication of the isomerization catalyst, provide strength and reduce fabrication costs. The binder should be uniform in composition and relatively refractory to the conditions used in the process. Suitable binders include inorganic oxides such as one or more of alumina, aluminum phosphate, magnesia, zirconia, chromia, titania, boria and silica. The catalyst also may contain, without so limiting the composite, one or more of (1) other inorganic oxides including, but not limited to, beryllia, germania, vanadia, tin oxide, zinc oxide, iron oxide and cobalt oxide; (2) non-zeolitic molecular sieves, such as the aluminophosphates of U.S. Pat. No. 4,310,440, the silicoaluminophosphates of U.S. Pat. No. 4,440,871 and ELAPSOs of U.S. Pat. No. 4,793,984; and (3) spinels such as $MgAl_2O_4$, $FeAl_2O_4$, $ZnAl_2O_4$, $CaAl_2O_4$, and other like compounds having the formula $MO-Al_2O_3$ where M is a metal having a valence of 2; which components can be added to the composite at any suitable point.

The catalyst may be prepared in any suitable manner. One method for preparation involves combining the binder and molecular sieve in a hydrosol and then gelling the mixture. One method of gelling involves combining a gelling agent with the mixture and then dispersing the resultant combined mixture into an oil bath or tower which has been heated to elevated temperatures such that gellation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging and drying treatments in oil and in ammoniacal solution to further improve their physical characteristics. The resulting aged and gelled particles are then washed and dried at a relatively low temperature of about 100° to 150° C. and subjected to a calcination procedure at a temperature of about 450° to 700° C. for a period of about 1 to 20 hours.

The combined mixture preferably is dispersed into the oil bath in the form of droplets from a nozzle, orifice or rotating disk. Alternatively, the particles may be formed by spray-drying of the mixture at a temperature of from about 425° to 760° C. In any event, conditions and equipment should be selected to obtain small spherical particles; the particles preferably should have an average diameter of less than about 5.0 mm, more preferably from about 0.2 to 3 mm, and optimally from about 0.3 to 2 mm.

Alternatively, the catalyst may be an extrudate. A multitude of different extrudate shapes are possible, including, but not limited to, cylinders, cloverleaf, dumbbell and symmetrical and asymmetrical polylobates. The extrudates may be further shaped to any desired form, such as spheres, by any means known to the art.

The catalyst of the present invention may contain a halogen component, comprising any of fluorine, chlorine, bromine or iodine or mixtures thereof, with chlorine being preferred. Preferably, however, the catalyst contains no added halogen other than that associated with other catalyst components.

The catalytic composite optimally is subjected to steaming to tailor its acid activity. The steaming may be effected at any stage of the zeolite treatment, but usually is carried out on the composite of zeolite binder prior to incorporation of the platinum-group metal. Alternatively or in addition to the steaming, the composite may be washed with one or more of a solution of ammonium nitrate, a mineral acid, and/or water.

Prior to addition of the hydrogenation metal component the composite preferably is ion-exchanged with a salt solution containing at least one hydrogen-forming cation such as $NH_4^+$ or quaternary ammonium. The hydrogen-forming cation replaces principally alkali-metal cations to provide, after calcination, the hydrogen form of the zeolite component.

Hydrogenation metal components are selected from the metals of Groups 6 to 10 of the Periodic Table (IUPAC), preferably molybdenum, rhenium and platinum-group metal. Preferred platinum-group metals include one or more of platinum, palladium, rhodium, ruthenium, osmium, and iridium. The preferred platinum-group metals are platinum and palladium, with platinum being especially preferred. The hydrogenation metal component may exist within the final catalyst composite as a compound such as an oxide, sulfide, halide, oxysulfide, etc., or as an elemental metal or in combination with one or more other ingredients of the catalyst composite. Where the hydrogenation metal component comprises platinum-group metal component, it is normally present in the catalyst in an amount of from about 10 to about 10,000 mass-ppm (parts per million) of the final catalyst composite, calculated on an elemental basis, with a level of about 100 to about 2000 mass-ppm being particularly suitable. When using a platinum component, very low levels of about 200 to 800 mass-ppm of platinum on the catalyst, on an elemental basis, are favored; levels of less than about 600 mass-ppm are especially favored and levels of about 300 to about 500 mass-ppm show excellent results. When using a palladium component, levels of about 400 to 2000 mass-ppm of palladium on the catalyst, on an elemental basis, are favored and levels of between about 500 and 1200 mass-ppm are especially favored. Where the hydrogenation metal comprises molybdenum, molybdenum is usually present in an amount of 0.1 to 5 mass-percent.

The hydrogenation metal component may be incorporated into the catalyst composite in any suitable manner. One method of preparing a platinum-group metal catalyst involves the utilization of a water-soluble, decomposable compound of a platinum-group metal to impregnate the calcined sieve/binder composite. Alternatively, a platinum-group metal compound may be added at the time of compositing the sieve component and binder. Yet another method of effecting a suitable metal distribution is by compositing the metal component with the binder prior to co-extruding the sieve and binder. Complexes of platinum-group metals which may be employed according to the above or other known methods include chloroplatinic acid, chloropalladic acid, ammonium chloroplatinate, bromoplatinic acid, platinum trichloride, platinum tetrachloride hydrate, platinum dichlorocarbonyl dichloride, tetraamineplatinum chloride, dinitrodiaminoplatinum, sodium tetranitroplatinate (II), palladium chloride, palladium nitrate, palladium sulfate, diaminepalladium (II) hydroxide, tetraaminepalladium (II) chloride, and the like.

It is within the scope of the present invention that the catalyst may contain other metal components known to modify the effect of the platinum-group metal component. Such metal modifiers may include without so limiting the invention rhenium, tin, germanium, lead, cobalt, nickel, indium, gallium, zinc, and mixtures thereof. Catalytically effective amounts of such metal modifiers may be incorporated into the catalyst by any means known in the art to effect a homogeneous or stratified distribution.

After addition of the metal component, the resultant catalytic composite usually is dried and then calcined, e.g., at a temperature of from about 400° to about 600° C. in an air atmosphere for a period of from about 0.1 to 10 hours.

The calcined composite optimally is subjected to a substantially water-free reduction step to insure a uniform and finely divided dispersion of the optional metallic components. The reduction optionally may be effected on the catalyst as loaded in the isomerization-process reactor of the present invention prior to the startup of the isomerization process. Substantially pure and dry hydrogen (i.e., less than 20 vol. ppm $H_2O$) preferably is used as the reducing agent in this step. In some cases the resulting reduced catalyst composite may also be beneficially subjected to presulfiding by a method known in the art to incorporate in the catalyst composite from about 0.01 to about 0.5 mass-percent sulfur, calculated on an elemental basis, into the catalyst.

The gradual accumulation of coke and other deactivating carbonaceous deposits on the catalyst during the operation of the isomerization process will eventually reduce the activity and selectivity of the process to a level such that regeneration is desirable. When the performance of the catalyst has decayed to the point where it is desired to regenerate the catalyst, the introduction of the hydrocarbon charge stock into the conversion zone containing the catalyst is stopped and the conversion zone purged with a suitable gas stream. Any suitable regeneration method may be used to restore catalyst activity and selectivity, either in situ or by unloading and regenerating the catalyst in an off-line facility.

With respect to the drawings, FIG. 1 depicts an apparatus generally designated as 100 for recovery of para-xylene from a xylene mixture. A feedstream containing a mixture of xylenes, ethylbenzene and heavier aromatics is supplied by line 102 to xylene distillation column 104 which provides a bottoms stream containing heavier aromatics which is withdrawn via line 106. An overhead from xylene column 104 contains xylenes and ethylbenzene and is passed via line 108 to para-xylene separation unit 110. Para-xylene separation unit 110 may be based on a fractional crystallization process or an adsorptive separation process, both of which are well known in the art, and preferably is based on the adsorptive separation process. A para-xylene rich stream is withdrawn from para-xylene separation unit 110 via line 112 for further product recovery.

A non-equilibrium mixture of xylenes and ethylbenzene is passed via line 114 to isomerization reactor assembly 116. Isomerization reactor assembly 116 may contain one or more reaction zones that serve to convert ethylbenzene and isomerize the non-equilibrium mixture of xylenes. The isomerization product is passed via line 118 from isomerization reactor assembly 116 to benzene column 120. Benzene column 120 is adapted to provide an overhead comprising lights which is removed via line 122 and a benzene rich fraction that is passed via line 124 to isomerization reactor assembly 116. A portion of the benzene is removed from line 124 via line 126 so that the concentration of benzene in the feed to the isomerization reactor assembly is maintained within a desired range.

Returning to benzene column 120, a bottoms stream is withdrawn via line 128 and passed to toluene column 130. The bottoms stream contains xylenes, remaining ethylbenzene, toluene and heavier by-products from the isomerization and ethylbenzene conversion. Toluene is recovered in an overhead fraction that is withdrawn via line 132 and a bottoms stream containing the $C_8$ aromatics and other higher boiling hydrocarbons, is passed via line 134 to xylene column 104.

Figure 2:
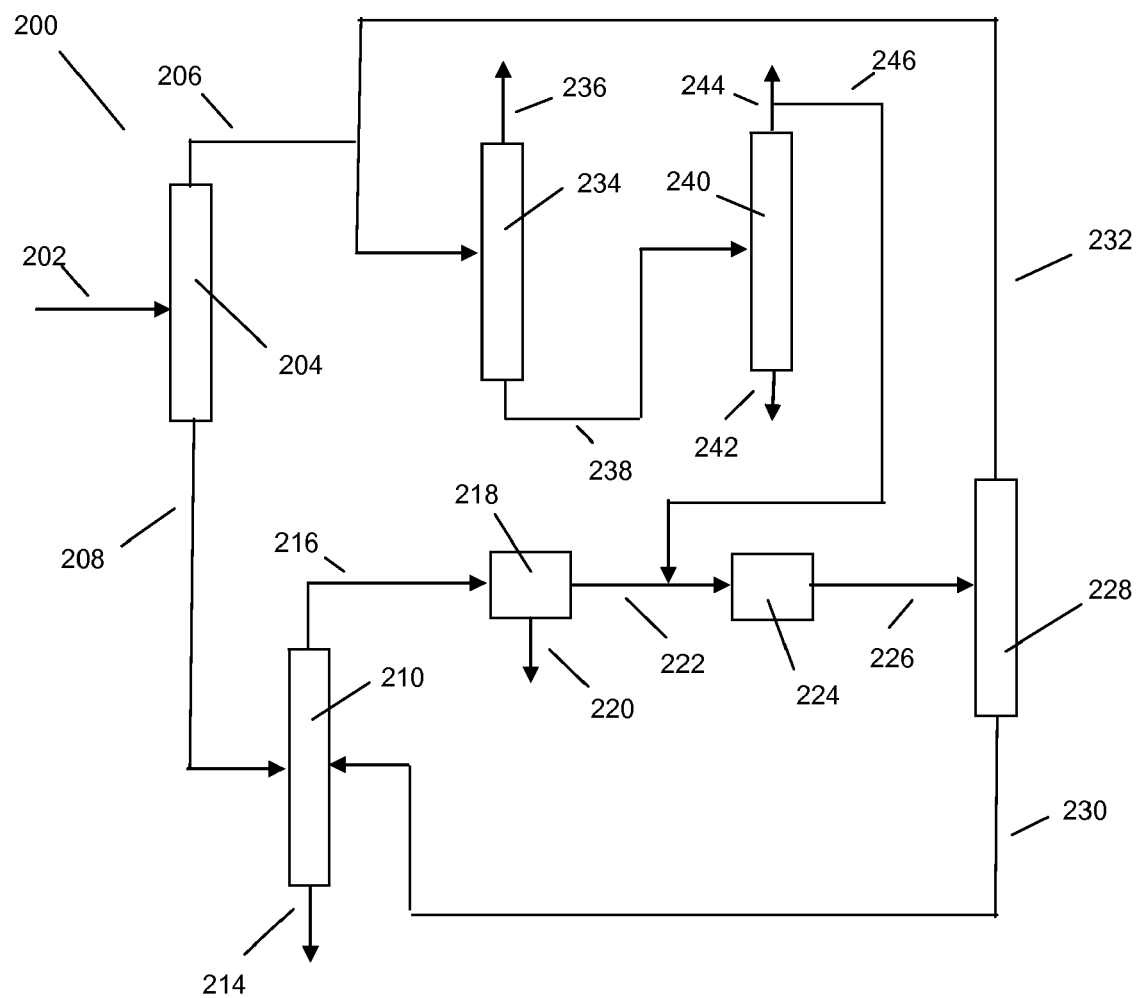
FIG. 2 is a schematic depiction of an apparatus of this invention in which benzene from the isomerization product is recovered and purified in a distillation assembly associated with recovery of benzene from feedstreams.

The apparatus of FIG. 2, which is generally designated as 200, illustrates the use of equipment used to treat portions of the feedstock for an aromatics unit. An aromatics-containing fraction, e.g., from a reformer, is passed via line 202 to splitter 204 that provides an overhead containing toluene and lighter hydrocarbons which overhead is withdrawn via line 206. Splitter 204 also provides a bottoms stream containing xylene, ethylbenzene and other higher boiling hydrocarbons. This bottoms stream is fed to xylene column 210 via line 208. A bottoms stream containing heavier hydrocarbons is withdrawn from xylene column 210 via line 214.

Xylene column 210 provides an overhead containing xylenes and ethylbenzene that is passed through line 216 to para-xylene separation unit 218. Para-xylene is withdrawn from the para-xylene separation unit 218 via line 220, and a non-equilibrium mixture of xylenes and ethylbenzene is withdrawn via line 222 and passed to isomerization reactor assembly 224 to provide an isomerized product that has a reduced amount of ethylbenzene. The isomerized product is then sent to toluene distillation assembly 228 which provides a bottoms stream containing xylene, ethylbenzene and higher boiling hydrocarbons and an overhead containing toluene, benzene and lower boiling hydrocarbons. The bottoms stream is passed via line 230 to xylene column 210.

The overhead from toluene distillation assembly 228 is passed via line 232 to lights column 234. As shown, the overhead from splitter 204 is also passed to lights column 234 via line 206. An overhead containing lights, i.e., hydrocarbons having boiling points less than benzene, is provided by lights column 234 and is withdrawn via line 236. A bottoms stream containing benzene and toluene is withdrawn from lights column 234 via line 238 and is passed to benzene column 240. Benzene column 240 provides a bottoms stream containing toluene which is removed by line 242. This bottoms stream may yield a toluene product or be used in a further reaction to produce additional xylenes such as a disproportionation or transalkylation reaction.

The overhead from benzene column 240 contains benzene which is withdrawn via line 244, with a portion being directed via line 246 to isomerization reactor assembly 224.

EXAMPLES

The following examples are presented only to illustrate certain specific embodiments of the invention, and should not be construed to limit the scope of the invention as set forth in the claims. There are many possible other variations, as those of ordinary skill in the art will recognize, which are within the spirit of the invention. All parts and percentages are by mass unless otherwise noted or clear from the context.

Example I

In this example an isomerization catalyst comprising approximately 400 mass-ppm platinum and about 67 mass percent MFI-type molecular sieve. The catalyst is prepared as follows: Steamed and calcined aluminum-phosphate-bound MFI zeolite spheres are prepared using the method of Example I in U.S. Pat. No. 6,143,941. The pellets are impregnated with an aqueous solution of tetra-amine platinum chloride to give 0.037 mass-percent platinum after drying and calcination at 538° C. The calcined catalyst is reduced in hydrogen at 425° C.

The catalyst is used in a pilot plant processing non-equilibrium $C_8$-aromatic feed having the following composition: $C_8$ aromatic component of about 7.3 mass-percent ethylbenzene, 0.7 mass-percent para-xylene, 69.8 mass-percent meta-xylene and 22.1 mass-percent ortho-xylene; and benzene for some runs as shown in Table 1.

The reaction conditions in the pilot plant include a pressure of about 1200 kPa gauge, a hydrogen to hydrocarbon mole ratio of about 4:1, and a weight hourly space velocity of 10 $hr^{-1}$. The reactor temperature is varied to provide various ethylbenzene conversions. A summary of the results are provided in Table 1.

TABLE 1

| Run | Benzene mass parts per 100 parts of xylenes | Temp, °C. | Xylene Product p-xylene to total xylenes | Ethylbenzene Conversion % | Xylene Ring Loss, mass % | TMB/$C_8$A |
|---|---|---|---|---|---|---|
| 1 | 0 | 404 | 23.7 | 74.6 | 2.1 | 0.0079 |
| 2 | 0 | 393 | 23.7 | 68.4 | 1.66 | 0.0062 |
| 3 | 0 | 382 | 23.6 | 54.2 | 1.43 | 0.0050 |
| 4 | 0 | 371 | 23.6 | 43.8 | 1.16 | 0.0041 |
| 5 | 18.9 | 404 | 23.7 | 71.9 | 1.60 | 0.0059 |
| 6 | 18.9 | 393 | 23.7 | 61.6 | 1.18 | 0.0049 |
| 7 | 18.9 | 382 | 23.6 | 51.7 | 0.95 | 0.0043 |

At this level of benzene addition, xylene ring loss and trimethylbenzene coproduction are both reduced as compared to substantially the same process but without the added benzene. The ethylbenzene conversion activity is reduced. As will be seen in the following example, at lower amounts of benzene addition, the ethylbenzene dealkylation activity is enhanced.

Example II

In this example, a catalyst of the type described in Example I is used in a pilot plant. A feed of substantially the same $C_8$ aromatic composition as in Example I is used for a number of runs with out added benzene or toluene and with additional benzene or toluene as set forth below in Table 2. The pilot plant is operated at a pressure of about 1200 kPa gauge, a hydrogen to hydrocarbon mole ratio of about 4:1, and a weight hourly space velocity of 10 $hr^{-1}$.

A summary of the runs is provided in Table 2. A number of analyses are conducted at each temperature and composition over a several hour period after the pilot plant has arrived at steady state conditions for each temperature and additive level. The analyses reported below are means.

TABLE 2

| Run | Added Benzene, Mass-% | Added Toluene Mass-% | Nominal WABT, °C. | pX/X, Weight ratio (×100) | Ethylbenzene, Conversion, Mass-% | Xylene Ring Loss, % | TMB, Mass-% |
|---|---|---|---|---|---|---|---|
| 1  | 0 | 0  | 371 | 23.56 | 43.6 | 1.93 | 0.47 |
| 2  | 0 | 0  | 382 | 23.69 | 54.6 | 2.12 | 0.55 |
| 3  | 0 | 0  | 393 | 23.73 | 65.5 | 2.44 | 0.66 |
| 4  | 0 | 0  | 404 | 23.76 | 75.7 | 2.87 | 0.82 |
| 5  | 5 | 0  | 363 | 23.82 | 50.8 | 1.17 | 0.62 |
| 6  | 5 | 0  | 381 | 23.87 | 70.4 | 1.77 | 0.92 |
| 7  | 5 | 0  | 396 | 23.85 | 84.3 | 2.88 | 1.32 |
| 8  | 8 | 0  | 368 | 23.82 | 52.5 | 0.60 | 0.46 |
| 9  | 8 | 0  | 386 | 23.84 | 71.9 | 1.18 | 0.75 |
| 10 | 8 | 0  | 400 | 23.81 | 84.4 | 2.16 | 1.13 |
| 11 | 0 | 5  | 371 | 23.60 | 44.3 | 1.63 | 0.44 |
| 12 | 0 | 5  | 382 | 23.72 | 55.7 | 1.81 | 0.52 |
| 13 | 0 | 5  | 393 | 23.76 | 66.9 | 2.07 | 0.60 |
| 14 | 0 | 5  | 404 | 23.79 | 76.9 | 2.41 | 0.71 |
| 15 | 0 | 10 | 371 | 23.50 | 36.5 | 0.99 | 0.28 |
| 16 | 0 | 10 | 382 | 23.67 | 49.5 | 1.26 | 0.35 |
| 17 | 0 | 10 | 393 | 23.76 | 63.7 | 1.43 | 0.44 |
| 18 | 0 | 10 | 404 | 23.82 | 76.1 | 1.73 | 0.56 |
| 19 | 0 | 20 | 371 | 23.45 | 32.4 | 0.31 | 0.20 |
| 20 | 0 | 20 | 382 | 23.60 | 40.2 | 0.37 | 0.21 |
| 21 | 0 | 20 | 393 | 23.72 | 53.3 | 0.61 | 0.26 |
| 22 | 0 | 20 | 404 | 23.79 | 67.8 | 0.76 | 0.34 |

As can be seen in the foregoing table, toluene at low concentrations has a little beneficial effect on ethylbenzene dealkylation and xylene isomerization activity, but that benefit is lost at higher toluene concentrations. In contrast, the runs with benzene show a pronounced effect on both ethylbenzene dealkylation and xylene isomerization activities at low concentrations. Reference can be made to table 1 where higher concentrations of benzene are used and at the higher concentrations, activity is suppressed.

Due to the increased catalytic activity achieved with the presence of small amounts of benzene, a lower temperature can achieve the same ethylbenzene conversion. Comparing equivalent ethylbenzene conversion, xylene ring loss is less with the presence of benzene than in the absence of benzene and toluene. As the amount of benzene is increased, the reduction in xylene loss and trimethylbenzene make is increased, but with some loss in activity as compared to lower benzene content feeds.

Example III

Several catalyst samples were prepared as follows.

Catalyst A: To a support material consisting of a 60 μm active layer of 50 wt % MFI zeolite (38Si/Al$_2$ ratio) and zirconia on an inert alpha alumina core (0.11 cm dia) was added an aqueous solution of tetra-ammine platinum chloride to give 0.01 mass-percent platinum after drying and calcination at 538° C. The calcined catalyst was reduced in hydrogen at 425° C.

Catalyst B: To a support material consisting of a 46 μm active layer of 50 wt % MFI zeolite (38Si/Al$_2$ ratio) and titania on an inert alpha alumina core (0.11 cm dia) was added an aqueous solution of tetra-ammine platinum chloride to give 0.01 mass-percent platinum after drying and calcination at 538° C. The calcined catalyst was reduced in hydrogen at 425° C.

Catalyst C: A support material consisting of 70 wt % active MFI zeolite (80Si/Al$_2$ ratio) extruded with silica was contacted with an aqueous solution of perrhenic acid to give 0.5 g Re per 100 grams of MFI-silica composition. After drying and calcination at 500° C. for 2 hours in air, the catalyst was reduced in hydrogen for 4 hours at 425° C. and sulfided with hydrogen sulfide to yield 0.13 mass-percent sulfur on the catalyst.

Catalyst D: The same support material consisting of 70 wt % active MFI zeolite (80Si/Al$_2$ ratio) extruded with silica used in Catalyst C was contacted with an aqueous solution of tetra-ammine platinum chloride to give 0.044 mass-percent platinum after drying and calcination at 538° C. The calcined catalyst was reduced in hydrogen at 425° C.

Example IV

Catalysts A, B, C and D were evaluated in a pilot plant for the isomerization of a feed stream (Feed 1) containing 7 mass-percent ethylbenzene, 1 mass-percent para-xylene, 22 mass-percent ortho-xylene and 70 mole-percent meta-xylene. The pilot plant runs were at a hydrogen to hydrocarbon ratio of 4:1, total pressure of 1200 kPa, and weight hourly space velocity of 10 based on the total amount of catalyst loaded. Conversion was varied by changing temperature. The pilot plant runs are summarized in Table 3, feed column 1. The product data was taken at approximately 50 hours of operation.

A second feed stream (Feed 2) was substituted into the pilot plant evaluation. It contained 90 mass-% of Feed 1 and 10 mass-% benzene. The product data that was taken with this feed stream appear in Table 3, feed column 2. For the catalysts tested, the yield of trimethylbenzene was reduced with the added benzene in the feed.

TABLE 3

| | | Catalyst | | | | | | |
|---|---|---|---|---|---|---|---|---|
| | % EB | A | | B | | C | | D | |
| Feed stream: | conversion | 1 | 2 | 1 | 2 | 1 | 2 | 1 | 2 |
| A9 + mass-% yield | 60% | 2.4 | 2.0 | 1.7 | 1.3 | 1.1 | 1.0 | 2.5 | 2.1 |
| | 70% | 2.6 | 2.1 | 1.8 | 1.4 | 1.5 | 1.2 | 2.8 | 2.4 |
| | 80% | 2.7 | 2.3 | 2.0 | 1.5 | 2.0 | 1.7 | 3.2 | 2.8 |

TABLE 3-continued

| | | Catalyst | | | | | | | |
|---|---|---|---|---|---|---|---|---|---|
| | | A | | B | | C | | D | |
| Feed stream: | % EB conversion | 1 | 2 | 1 | 2 | 1 | 2 | 1 | 2 |
| % Xylene loss | 60% | 5.5 | 6.0 | 4.5 | 4.5 | 2.4 | 3.1 | 4.0 | 4.7 |
| | 70% | 6.0 | 6.4 | 4.9 | 4.9 | 3.2 | 3.8 | 4.7 | 5.4 |
| | 80% | 6.4 | 7.1 | 5.3 | 5.3 | 4.6 | 5.0 | 6.6 | 7.0 |

The invention claimed is:

1. A process for the isomerization of a non-equilibrium feed mixture of xylenes comprising: adding to the feed mixture, a stream consisting essentially of benzene to provide a feed stream; contacting in the presence of hydrogen the feed stream with a catalyst selected from the group consisting of:
   a) a catalyst comprising a 46 micron to 60 micron active layer of MFI zeolite and zirconia or titania on an inert alpha alumina core and the catalyst further comprising a hydrogenation component selected from the group consisting of platinum, palladium, molybdenum, and rhenium;
   b) a catalyst comprising a MFI zeolite and silica support and a hydrogenation component selected from the group consisting of platinum, palladium, molybdenum, and rhenium; and
   c) mixtures thereof,
   under isomerization conditions to isomerize the xylenes and provide a product stream having a redistributed xylenes ratio, wherein the stream consisting essentially of benzene is added in an amount resulting in the feed stream comprising from about 0.5 to about 25 mass percent benzene.

2. The process of claim 1 wherein the feed mixture contains ethylbenzene and the feed stream containing benzene is subjected to ethylbenzene conversion conditions to provide a product stream having reduced ethylbenzene content.

3. The process of claim 2 wherein the ethylbenzene conversion conditions comprise ethylbenzene dealkylation conditions and at least a portion of the ethylbenzene is dealkylated.

4. The process of claim 3 wherein the ethylbenzene conversion conditions comprise the presence of pentasil zeolite-containing catalyst.

5. The process of claim 1 wherein the feed mixture contains ethylbenzene and ethylbenzene is subjected to ethylbenzene conversion conditions.

6. The process of claim 5 wherein the ethylbenzene conversion conditions comprise ethylbenzene dealkylation conditions.

7. The process of claim 6 wherein benzene is provided in an amount sufficient to reduce trimethylbenzene co-production.

8. The process of claim 5 wherein at least a portion of the benzene in the product stream is selectively recovered and a least a portion of the recovered benzene is used as provided benzene.

9. The process of claim 8 wherein the selective recovery of benzene is by distillation.

* * * * *